United States Patent [19]

Butterfield

[11] 4,447,229
[45] May 8, 1984

[54] TAMPER-RESISTANT HYPODERMIC SYRINGE

[75] Inventor: Ida M. Butterfield, Santa Maria, Calif.

[73] Assignee: Butterfield Group, Santa Maria, Calif.

[21] Appl. No.: 524,473

[22] Filed: Aug. 19, 1983

Related U.S. Application Data

[62] Division of Ser. No. 364,011, Mar. 31, 1982, abandoned.

[51] Int. Cl.$^3$ .............................................. A61M 5/00
[52] U.S. Cl. .................................................. 604/111
[58] Field of Search ............... 604/111, 110, 219, 221, 604/222, 218, 232

[56] References Cited

U.S. PATENT DOCUMENTS

| | | | |
|---|---|---|---|
| 1,561,854 | 11/1925 | Hein | 604/219 |
| 2,193,489 | 3/1940 | Nevin | 128/218 D |
| 2,592,381 | 4/1952 | Blackman | 128/218 P |
| 2,756,747 | 7/1956 | Axelrad | 604/219 |
| 2,994,323 | 8/1961 | Dann et al. | 128/218 D |
| 3,050,059 | 8/1962 | Wall et al. | 128/218 P |
| 4,221,218 | 9/1980 | Pfleger | 128/218 DA |

*Primary Examiner*—John D. Yasko
*Attorney, Agent, or Firm*—Daniel C. McKown

[57] ABSTRACT

Instances have been discovered in which a person has inserted the needle of a first hypodermic syringe through the soft rubber drive piston of a second hypodermic syringe to aspirate some of the narcotic fluid from the second syringe into the first syringe. To prevent this mode of pilfering, an impenetrable barrier is included in the second syringe to prevent the insertion of the needle of the first syringe. The impenetrable barrier may be a unitary portion of the screw that is normally included in the drive piston of the syringe, or the barrier may be a separate part molded into the drive piston.

2 Claims, 6 Drawing Figures

TAMPER-RESISTANT HYPODERMIC SYRINGE

This application is a division of application Ser. No. 364,011, filed Mar. 31, 1982 now abandoned.

BACKGROUND OF THE INVENTION

1. Field of the Invention

The present invention is in the field of medical apparatus and more specifically relates to an improvement in a hypodermic syringe to render the syringe more tamper-resistant.

2. The Prior Art

A fractional cross-sectional view through a portion of a syringe of the prior art is shown in FIG. 1. FIG. 1 shows the end of the hypodermic syringe that is opposite the end to which the needle is attached. As shown in FIG. 1, the hypodermic syringe includes a tubular member 12 of glass or other transparent material which serves to contain the fluid 14. A drive piston 16 of a soft rubber is included within the tubular member 12 and forms a slidable seal with the inside surface of the tubular member 12. A screw 18 is embedded in the drive piston 16 to permit an actuating rod (not shown) to be connected to the drive piston 16. The actuating rod facilitates application of a force, directed leftward in FIG. 1, to the drive piston 16 leftward for the purpose of expressing the fluid 14 from the syringe.

Instances have been discovered in which a person has inserted a needle 20 in the manner shown in FIG. 1 through the drive piston 16 to aspirate some of the fluid (narcotics). An object of the present invention is to prevent this type of pilfering.

SUMMARY OF THE INVENTION

In accordance with the present invention, an impenetrable barrier is included in the syringe to prevent the insertion of a needle in the manner shown in FIG. 1.

The novel features which are believed to be characteristic of the invention, both as to organization and method of operation, together with further objects and advantages thereof, will be better understood from the following description considered in connection with the accompanying drawings in which several embodiments of the invention are illustrated by way of example. It is to be expressly understood, however, that the drawings are for the purpose of illustration and description only and are not intended as a definition of the limits of the invention.

DETAILED DESCRIPTION

Figure 1:
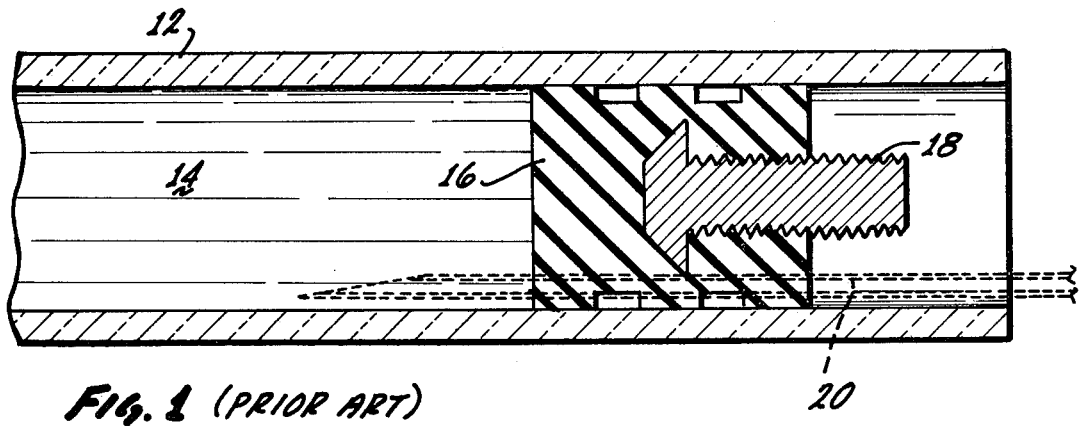
FIG. 1 is a fractional cross-sectional view showing a syringe of the prior art.

Turning now to the drawings, in which like parts are denoted by the same reference numeral throughout, there is shown in FIG. 1 a cross-sectional view of a portion of a hypodermic syringe of the type known in the prior art. Specifically, FIG. 1 shows the end of the syringe which is opposite to the end to which the needle is attached. As discussed above, this type of syringe is susceptible to pilfering in the manner shown in FIG. 1. That is, the needle 20 of a second hypodermic syringe is inserted through the rubber drive piston 16 and the fluid 14 is then aspirated from the first syringe into the second syringe. Thereafter, the needle 20 is removed from the first syringe, and in many cases, the theft remains undetected, particularly if care is taken to replace the pilfered fluid 14 with a saline solution or with water.

Clearly what is needed is some kind of a barrier that cannot be penetrated by the needle 20 of the second hypodermic syringe. Initially, the present inventor attempted to devise a cap that would fit tightly over the end of the tubular member 12. However, it was not possible to design a cap that would prevent tampering yet still be easily and rapidly removable by a legitimate user.

Another unsatisfactory approach considered by the inventor was to attach a washer to the screw 18 by means of a nut. This approach had two problems. First, the nut was exposed and therefore could also be tampered with and probably unscrewed. Secondly, the presence of the washer and the nut on the exposed portion of the screw 18 seriously reduced the length of the remaining threaded portion so that the actuator rod could not be adequately screwed on to the screw 18. Therefore, this second approach was deemed less attractive than the techniques later developed.

The present inventor found that it was necessary to give proper consideration to the fact that the rubber of which the drive piston 16 was formed is extremely soft, and also, the fact that the dimensions involved are quite small. For example, the bore of the tubular member 12 is typically only 7 millimeters. Thus, care must be taken that the modifications made to the drive piston 16 should not unduly weaken the remaining rubber portions, or interfere with the ability of the drive piston 16 to seal against the inside wall of the tubular member 12.

Figure 2:
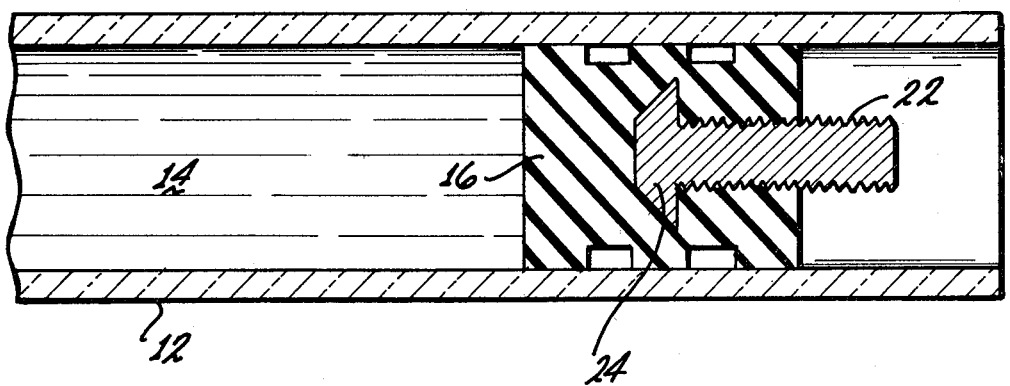
FIG. 2 is a fractional cross-sectional view showing an early embodiment of the syringe of the present invention.

FIG. 2 shows a first embodiment of the syringe in accordance with the present invention. In this first embodiment, the screw 18 of FIG. 1 has been replaced by the screw 22 of FIG. 2 which has a head of larger diameter. Initially it was thought that if the difference between the radius of the bore of the tubular member 12 and the radius of the screw head 14 were less than the diameter of the smallest needle, such as the needle 20 of FIG. 1, then the syringe of FIG. 2 would be pilfer-proof. However, the present inventor discovered that this criterion is not proper because the softness of the rubber of the drive piston 16 permits the screw 22 to be deflected laterally from the center line of the tubular member 12. Although some deflection was to be expected, the full extent of the deflection had not previously been appreciated. Accordingly, the present inventor discovered that a safer criterion is that the difference between the diameter of the bore of the tubular member 12 and the diameter of the screw head 24 should not exceed the diameter of the smallest needle that could be used to pilfer the contents of the syringe.

Although the design in FIG. 2 is workable, the present inventor recognized that the screw head 24 almost divides the drive piston 16 into two parts, and that the parts are connected only by a relatively thin band of the rubber of the drive piston 16 that extends circumferentially around the screw head 24 at its widest diameter. Thus, the embodiment of FIG. 2 is workable, but it is probably not as desirable an embodiment as the embodiments discussed below.

Figure 3:
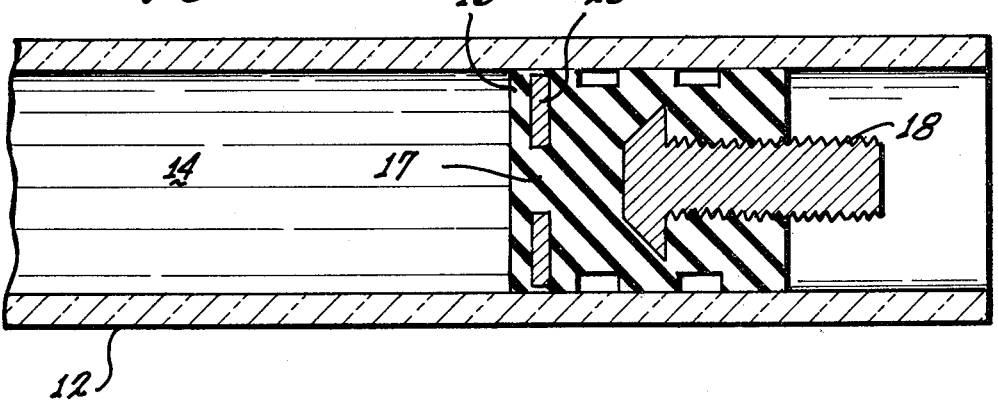
FIG. 3 is a fractional cross-sectional view showing a first preferred embodiment of the syringe of the present invention.

FIG. 3 shows a first preferred embodiment in which the screw 18 of FIG. 3 is comparable to the screw 18 of FIG. 1 used in the prior art. The embodiment of FIG. 3 is distinguished by the presence of a washer 26 that is embedded in the drive piston 16. It should be noted that a central portion 17 of the drive piston 16 of relatively large diameter connects the portions of the drive piston that lie on opposite sides of the washer 26. Accordingly, the strength of the drive piston 16 is not appreciably altered by the presence of the washer 26. Likewise, the portions of the drive piston 16 that lie on opposite sides of the head of the screw 18 are connected by an annular region of appreciable width, so that in this region the drive piston 16 of FIG. 3 is at least as strong as the corresponding region of the prior art drive piston shown in FIG. 1.

Figure 4:
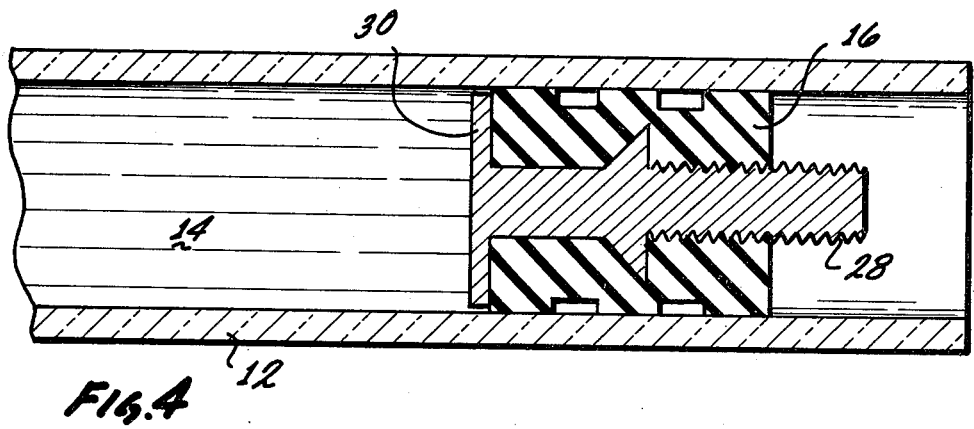
FIG. 4 is a fractional cross-sectional view showing a second preferred embodiment of the syringe of the present invention.

In the second preferred embodiment shown in FIG. 4, the screw 18 of FIG. 1 has been replaced by an improved screw 28 which extends through the drive piston 16 to terminate in a circular head 30 that is comparable to the head of a nail. It should be noted that the structure of the screw 28 shown in FIG. 4 not only does not weaken the drive piston 16, but instead, actually reduces the stresses on the rubber, at least when the drive piston is drawn to the right as viewed in FIG. 4. As discussed above in connection with the embodiment of FIG. 2, the inventor has found that the difference between the diameter of the bore of the tubular member 12 and the diameter of the circular head 30 should not exceed the diameter of the smallest needle that might be used to aspirate the contents of the syringe.

Figure 5:
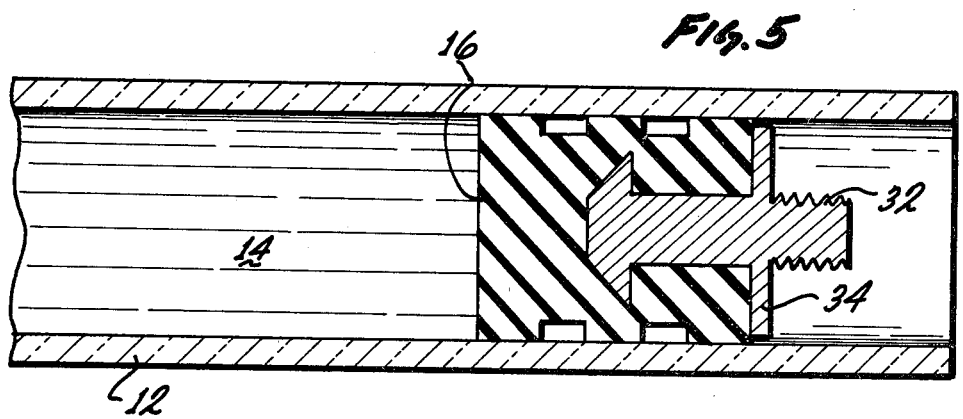
FIG. 5 is a fractional cross-sectional view showing a third preferred embodiment of the syringe of the present invention; and, FIG. 6 is a fractional cross-sectional view showing an alternative embodiment of the syringe of the present invention.

FIG. 5 shows a third preferred embodiment of a syringe in accordance with the present invention. In the embodiment of FIG. 5, the screw 18 of FIG. 1 is replaced by the screw 32 of FIG. 5. The screw 32 includes an integral disc 34 which serves as an impenetrable barrier. When the drive piston 16 is pushed to the left in FIG. 5, the disc 34 distributes the force more or less uniformly over the right hand end of the drive piston 16, thereby relieving the stresses that would otherwise develop in the region of the head of the screw 32. Consistent with the above discussions, the diameter of the integral disc 34 should not be less than the diameter of the tubular member 12 by an amount exceeding the diameter of the smallest needle that might be used to pilfer the contents of the syringe.

Figure 6:
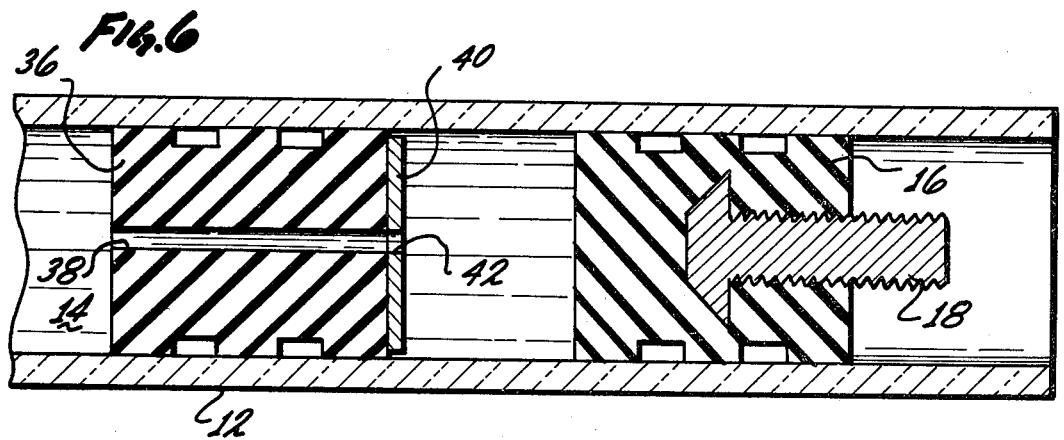

FIG. 6 shows an embodiment of the present invention that is intended for use with a syringe having, in addition to the normal drive piston 16, a non-retractable stopper 36 having a longitudinal passage 38.

In the known prior use of such a syringe, as the drive piston 16 is pushed to the left as viewed in FIG. 6, it pushes the non-retractable stopper 36 along in front of it. However when the drive piston 16 is retracted to the right, the non-retractable stopper 36 remains at its most advanced position. The longitudinal passage 38 permits some of the fluid 14 to flow through the non-retractable stopper 36 into the space between the drive piston 16 and the non-retractable stopper. In this manner, the non-retractable stopper serves as an indicator of whether the drive piston 16 has ever been advanced.

Initially, the drive piston 16 and the non-retractable stopper 36 are in end-to-end contact, and it is not impossible for a thief to insert a thin hypodermic needle through both the drive piston 16 and the non-retractable stopper 36 to pilfer the fluid 14. Clearly, the measures shown in FIGS. 2–5 would prevent such pilfering. The embodiment shown in FIG. 6 would not prevent pilfering but would leave a visible indication that the syringe has been tampered with, and would have the added advantage of requiring no modification whatsoever to the drive piston 16 and the screw 18 currently in use. In the embodiment of FIG. 6, an impenetrable washer 40 is bonded to one end of the non-retractable stopper 36. In FIG. 6, the washer 40 is bonded to the end of the non-retractable stopper that faces the drive piston 16. With the impenetrable washer 40 in place, any attempt to pilfer the fluid 14 will result in the non-retractable stopper 36 being advanced to the left as viewed in FIG. 6 where the non-retractable stopper 36 will remain to serve as a signal that the syringe has been tampered with. Further, as discussed above, the difference between the diameter of the bore of the tubular member 12 and the diameter of the impenetrable washer 40 should not exceed the diameter of the smallest needle that could be used to pilfer the fluid 14.

Thus, there have been described several embodiments of an invention which should materially reduce the pilferage of narcotics and other fluids from hypodermic syringes by penetration of the drive piston by the neelde of a second hypodermic syringe. In each of these embodiments described herein, an impenetrable barrier is placed in the path of the needle of the second hypodermic syringe to deny access of that needle to the fluid within the syringe.

The foregoing detailed description illustrates several embodiments of the invention, and it is to be understood that additional embodiments thereof will be obvious to those skilled in the art. The embodiments described herein together with those additional embodiments are considered to be within the scope of the invention.

What is claimed is:

1. A tamper-resistant hypodermic syringe comprising in combination:
   a tubular member having a proximal end which is unobstructed and having a distal end;
   a drive piston positioned within said tubular member;
   a non-retractable stopper having a longitudinal passage to permit the syringe to be used for aspiration, said non-retractable stopper located within said tubular member immediately adjacent the distal side of said drive piston, but not connected to said drive piston;
   a barrier impenetrable by a hypodermic needle and affixed to said non-retractable piston whereby the attempted insertion of a hypodermic needle through said non-retractable piston from the proximal end of said tubular member will cause said non-retractable stopper to be pushed toward the distal end, thereby giving a visual indication that the syringe has been tampered with.

2. The improved drive piston of claim 1 wherein the difference between the diameter of the bore of the tubular member and the diameter of said head portion does not exceed the diameter of the smallest hypodermic needle that could be used to pilfer the contents of the hypodermic syringe.

* * * * *